United States Patent [19]

Rosen

[11] Patent Number: 5,232,364

[45] Date of Patent: Aug. 3, 1993

[54] DENTAL CROWN ANALOG FOR ORTHODONTIC ANCHORAGE

[76] Inventor: David B. Rosen, 9 Trodden Path, Lexington, Mass. 02173

[21] Appl. No.: 937,144

[22] Filed: Aug. 31, 1992

[51] Int. Cl.⁵ .......................... A61C 8/00; A61C 3/00
[52] U.S. Cl. ........................ 433/173; 433/8; 433/9
[58] Field of Search .............. 433/173, 174, 8, 9, 433/10, 17, 172

[56] References Cited

U.S. PATENT DOCUMENTS

| | | | |
|---|---|---|---|
| 3,932,940 | 1/1976 | Andren | 433/9 |
| 4,015,334 | 4/1977 | Moss | 433/9 X |
| 4,083,113 | 4/1978 | Miller et al. | 433/17 |
| 4,094,068 | 6/1978 | Schinhauser | 433/9 |
| 4,722,689 | 2/1988 | Corbett | 433/17 X |
| 4,773,857 | 9/1988 | Herrin | 433/9 X |
| 4,988,292 | 1/1991 | Rosen | 433/173 X |
| 5,015,186 | 5/1991 | Detsch | 433/173 |
| 5,071,345 | 12/1991 | Rosen | 433/173 X |
| 5,082,442 | 1/1992 | Rosen | 433/173 X |

*Primary Examiner*—Gene Mancene
*Assistant Examiner*—Nicholas D. Lucchesi
*Attorney, Agent, or Firm*—Alfred H. Rosen

[57] ABSTRACT

A support plate for an orthodontic anchorage fitting designed to be removably attached to a dental crown analog. The plate has curved slots at each end for passage of screws used to attach it to a sidewall of the analog, so that the plate can be adjusted on the sidewall around an axis that is between the slots. Pivot means can be provided in the sidewall and the plate for locating the plate pivotally on the sidewall. The plate is made of a material, such as stainless steel, to which an orthodontic anchorage fitting may be attached by welding.

19 Claims, 2 Drawing Sheets

DENTAL CROWN ANALOG FOR ORTHODONTIC ANCHORAGE

This invention relates in general to the dental field of orthodontics, and more particularly to a dental crown analog for orthodontic anchorage to a dental implant fixture in a patient who is edentulous at the site where such anchorage is desired. This invention is related to the inventions of my U.S. Pat. Nos. 4,988,292; 5,071,345 and 5,082,442; the disclosures of which are incorporated herein by reference.

BACKGROUND OF THE INVENTION

In one class of systems used in orthodontic practice archwires cooperating with brackets affixed to buccal or lingual surfaces of teeth are used to adjust the relative positions in a dental arch with appropriate forces applied over time to individual teeth in the arch. These wires are anchored at their ends to tubes and the like affixed to the patient's molars, pre-molars and other suitable teeth. In cases of patients who have lost their molars or pre-molars, or otherwise lack suitable anchorage, the use of molar tubes and the like has not been available to orthodontists. Recent developments in the art of dental implantology now provide a variety of artificial root fixtures, notably the endosseous implant fixture, which provide an opportunity to fill that need for the partially edentulous patient. The inventions of my above-referenced patents introduce a new system and a variety of pre-fabricated components which facilitate orthodontic anchorage to a dental implant fixture installed at an edentulous site. My present invention further improves dental crown analogs intended for use in my new system.

GENERAL NATURE OF THE INVENTION

A dental implant fixture in the class of endosseous implant fixtures consists essentially of an elongated body implanted in the patient's jawbone and having an elongated socket for receiving a fitting or fittings which can be used to fix a prosthodontic restoration on the implant fixture. Commonly, the socket is an internally-threaded receiving bore, and the restoration is fixed to the implanted fixture with a bolt threaded into that bore. Other forms of dental implant fixtures are in use, and a wide variety of materials are used to make them. This invention is disclosed in connection with the endosseous implant fixture as currently known to be in use, as a best mode now known to practice the invention. It will be understood that the invention is not limited to the details of the illustrative disclosure; to the contrary, the invention is intended for use with any and all substitutes for natural tooth structures that are capable of providing the required anchorage, whether presently known or made available in the future.

Control of dental plaque, consisting of bacteria, is a very important factor in the general health of the soft and hard tissue which supports the teeth. If bacterial plaque is allowed to accumulate in the gingival sulcus it will result in gingival inflammation and bone loss in the affected area. This becomes particularly important during the process of orthodontic therapy. The mechanical brackets, bands and other attachments heretofore used by orthodontists to affix molar tubes and the like to teeth can serve as plaque-retentive sites that require extra effort on the part of the patient to keep them clean and prevent periodontal disease.

Orthodontic therapy typically takes 1-2 years, during which time it is imperative to maintain the highest level of oral hygiene. My present invention incorporates a design that is characterized by a maximum of smooth tooth surfaces, in order to minimize plaque retention.

During the process of orthodontic therapy there is a constant process of remodeling of the bone surrounding the teeth being moved. Bone is resorbed on the pressure side of the teeth being moved and bone is deposited on the tension side of the same teeth. Bacterial plaque can interfere with this process. The presence of inflammation, which is in response to the bacterial deposits, inhibits the process of bony deposition during tooth movement. This can result in a tooth being moved and bone being resorbed on the pressure side with no simultaneous repair at the site being vacated by the tooth. When a dental implant fixture is involved such an accumulation of bacterial plaque can result in loss of osseointegration and a subsequent loosening and failure of the implant—a disastrous result. It is an object of this invention to provide an environment that is easily cleaned by the patient during the process of orthodontic therapy and to minimize the accumulation of bacterial plaque in that environment.

GENERAL NATURE OF THE INVENTION

In accordance with my above-mentioned U.S. Pat. No. 4,988,292 an abutment for orthodontic anchorage is mountable on a dental implant fixture in the same manner as components used to support a prosthodontic restoration. This abutment is adjustable around the axis of the implant fixture, and it supports a mount for holding an orthodontic anchor fixed to a buccal or lingual side of the abutment, which mount is adjustable around an axis running between the buccal and lingual surfaces. The present invention teaches an improvement in the invention of my '292 patent.

In accordance with my present invention a commonly-available anchoring device, for example, a molar tube, is removably attachable directly to a lingual or buccal wall of a dental crown analog in a manner that allows the anchoring device to be adjusted around an axis extending between the lingual and buccal walls of said crown analog. The crown analog preferably has an exterior size and contour to approximate the dimensions and shape of a natural tooth at the site where the orthodontic anchorage is desired. The removable attachment of the anchoring device to the crown analog is rigid and mechanical without requiring glue or cement of any kind. It can be loosened and adjusted around the above-said axis, and retightened with ease.

The invention will be described in greater detail with reference to the accompanying drawings, which illustrate the invention in general terms and in terms of a specific embodiment.

DETAILED DESCRIPTION OF THE DRAWINGS

Figure 1:
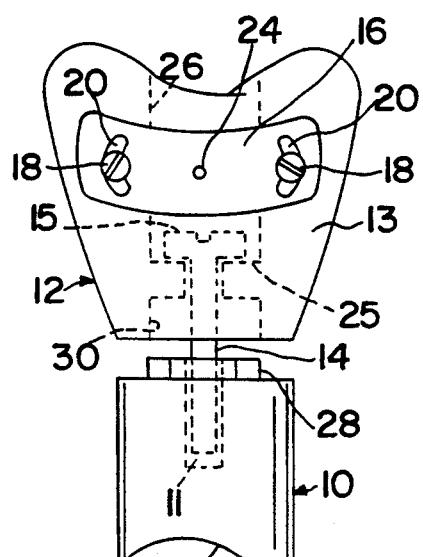
FIG. 1 is a mesio-distal view of a generalized illustration of the invention.
Figure 2:
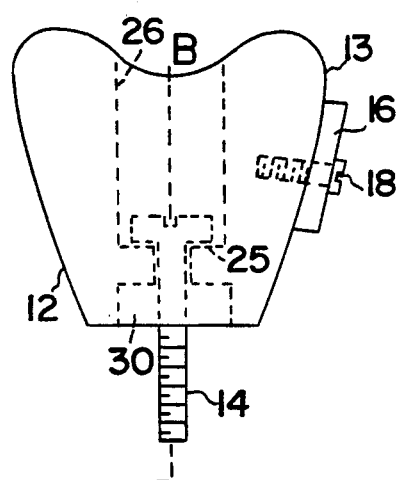
FIG. 2 is a buccalingual view of FIG. 1.
Figure 3:
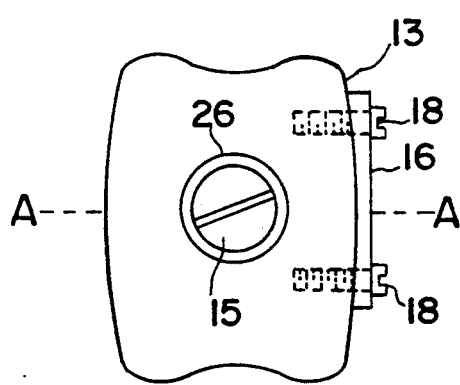
FIG. 3 is an occlusal view of FIG. 1.
Figure 3A:
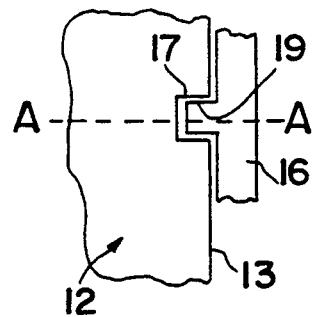
FIG. 3A is an enlarged view of a part of FIG. 3.

FIGS. 1 to 3, inclusive, show a typical dental implant fixture 10 to which a dental crown analog 12 may be affixed with a bolt 14. An orthodontic plate 16 is removably fixed to the crown analog 12 at one side surface 13, which may be labial or lingual, by means of screws 18 passing through curved slots 20 and threaded into the body of the crown analog. The curved slots allow the plate 16 to be adjusted on the surface 13 around an axis A—A shown in FIG. 3 and represented by a dot 24 in FIG. 1; this is done by loosening the screws 18, adjusting the plate 16, and retightening the screws. A socket-depression 17 may be provided in the surface 13 coaxial with the axis A—A, to receive a locating pin 19 of the plate 16, as is best shown in FIG. 3A. An orthodontic anchorage fixture (not shown) may be attached to the plate 16, as by spot-welding, to which end the plate may desirably be made of stainless steel. In known fashion, the crown analog has a bore 26 through it from its occlusal end to its gingival end through which the bolt 14 is fitted into an internally-threaded bore 11 in the implant fixture 10. The bolt has a head 15 which engages a shelf 25 at the gingival end of the bore 26 to tighten the crown analog on the implant fixture.

The crown analog and the implant fixture may have interfitting anti-rotation devices 30 and 28, respectively, which allow the crown analog to be rotationally adjusted around a common longitudinal axis B—B relative to the implant fixture, and to be locked in a selected adjustment. Thus, the plate 16 may be adjusted to and locked in a desired position around each of the axes A—A and B—B.

Figure 4:
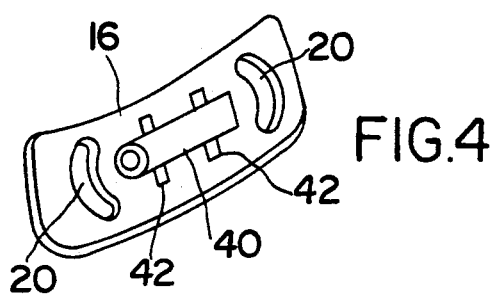
FIG. 4 illustrates an orthodontic bracket modified for use in the invention.
Figure 5:
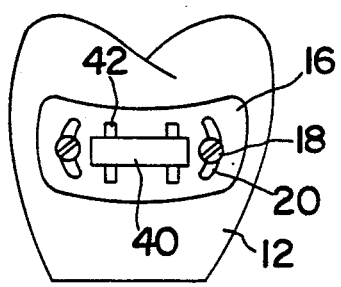
FIG. 5 is a mesial-distal view of the invention fitted with the bracket of FIG. 4.
Figure 6:
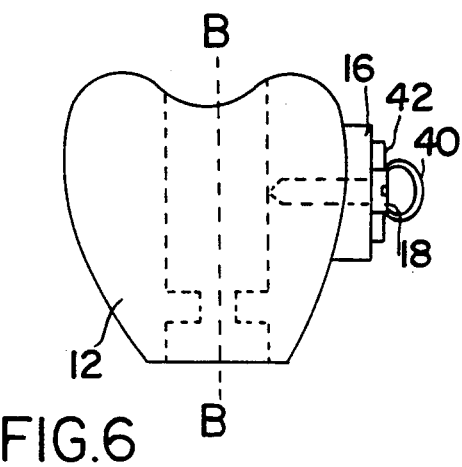
FIG. 6 is a buccalingual view of FIG. 5.
Figure 7:
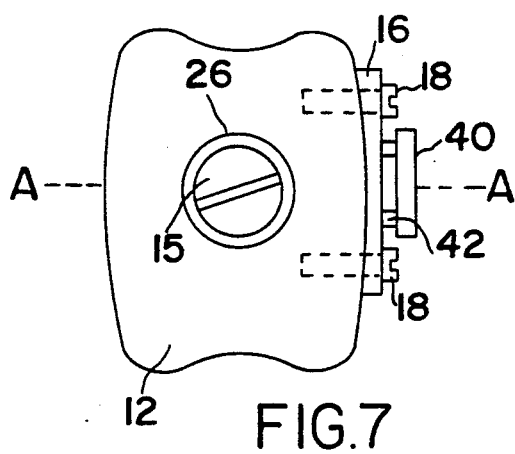
FIG. 7 is an occlusal view of FIG. 5.

FIG. 4 shows a molar tube 40 fixed to the plate 16 with tubes 42. The tube 40 and tubes 42 may be fixed together by welding, and the tabs may be tack-welded to the plate 16. Alternatively, an available molar tube fitting may be modified to include the slots 20 and the locating pin 19. The combined fitting, plate 16 and molar tube 40, may then be affixed to the side 13 of the crown analog 12, as is illustrated in FIGS. 5, 6 and 7, wherein parts similar to parts in FIGS. 1, 2 and 3 bear like reference characters. I have thus shown and described a new and simplified dental crown analog for orthodontic anchorage which is easy to keep clean, easy to install and adjust, and inexpensive to make and which attaches directly to a side of an artificial tooth without the need for bands or glues. In recognition of tack-welding as a skill of orthodontic practitioners, a variety of orthodontic fittings may be tack-welded to the plate 16.

I claim:

1. A dental crown analog for orthodontic anchorage comprising in combination a prefabricated dental abutment having labial and lingual sides, a support plate for an orthodontic anchorage and mechanical means including two separate elongated slots to removably affix said plate directly to at least two spatially separated locations on an exterior surface of one of said sides, said means to affix permitting adjustment of said plate around an axis which extends between said sides.

2. A combination according to claim 1 including means to locate said plate rotatably around said axis.

3. A combination according to claim 1 in which said means to affix include screw means threadable directly into the body of said abutment.

4. A combination according to claim 3 wherein said slots are substantially arcuate and said screw means are engaged in said slots, 5. A combination according to claim 4 slots are located opposite each other approximately on the locus of a circle and a screw means is engaged in each slot and is threaded directly into the body of said analog.

6. A combination according to claim 5 including an orthodontic anchorage fitting affixed to said plate.

7. A combination according to claim 6 in which said plate is made of a metal to which said fitting can be welded.

8. A combination according to claim 6 in which said fitting is a molar tube.

9. A combination according to claim 1 including an orthodontic anchorage fitting affixed to said plate.

10. A combination according to claim 9 in which said plate is made of a metal to which said fitting can be welded.

11. The invention according to claim 1 in which said axis is between said locations 12. An orthodontic anchorage device comprising a substantially flat base, an orthodontic fitting affixed to said base, and at least two substantially arcuately curved elongated slots on said base extending through said base for passage of means to affix said base adjustably to a surface of another body.

13. An anchorage device according to claim 12 in which said slots are each curved on the locus of a circle and each slot is totally enclosed within said base.

14. An anchorage device according to claim 13 in which said slots lie in opposite locations substantially on the locus of said circle.

15. An anchorage device according to claim 14 including locating means at the center of said circle.

16. An anchorage device according to claim 12 in combination with an artificial tooth in which said base is fixed to a side wall of said tooth with screws passing through said slots and threaded into the body of said tooth, for adjustably fixing said base to said tooth in a position that is adjustable rotatably around an axis that is substantially perpendicular to said base.

17. A combination according to claim 16 including interfittingly locating means on said surface and said base for locating said base rotatably around said axis, 18. An anchorage device according to claim 12 in which said orthodontic fitting is a molar tube.

19. An anchorage device according to claim 18 in which said molar tube extends between said slots.

* * * * *